(12) United States Patent
Ward et al.

(10) Patent No.: US 7,368,056 B2
(45) Date of Patent: May 6, 2008

(54) PRODUCTION OF POTABLE LIQUIDS

(75) Inventors: Robert S. Ward, Lafayette, CA (US); Sallie K. Coviello, San Francisco, CA (US)

(73) Assignee: The Polymer Technology Group, Incorporated, Berkeley, CA (US)

( * ) Notice: Subject to any disclaimer, the term of this patent is extended or adjusted under 35 U.S.C. 154(b) by 680 days.

(21) Appl. No.: 10/754,508

(22) Filed: Jan. 12, 2004

(65) Prior Publication Data

US 2004/0140264 A1 Jul. 22, 2004

(51) Int. Cl.
*B01D 63/08* (2006.01)
*B65D 85/808* (2006.01)
*B01D 61/00* (2006.01)
*B65D 85/00* (2006.01)

(52) U.S. Cl. ............... 210/500.21; 210/500.27; 210/500.36; 210/502.1; 210/640; 210/644; 210/649; 210/652; 426/115; 426/120

(58) Field of Classification Search ............ None
See application file for complete search history.

(56) References Cited

U.S. PATENT DOCUMENTS

| | | | |
|---|---|---|---|
| 4,157,085 A | | 6/1979 | Austad |
| 4,686,137 A | * | 8/1987 | Ward et al. ............ 442/76 |
| 4,879,030 A | * | 11/1989 | Stache ................ 210/238 |
| 4,904,260 A | | 2/1990 | Ray et al. |
| 4,920,105 A | * | 4/1990 | Zelman .................. 514/59 |
| 5,005,591 A | | 4/1991 | Austad |
| 5,047,055 A | | 9/1991 | Bao et al. |
| 5,192,326 A | | 3/1993 | Bao et al. |
| 5,358,732 A | * | 10/1994 | Seifter et al. ............ 426/592 |
| 5,428,123 A | | 6/1995 | Ward et al. |
| 5,589,563 A | | 12/1996 | Ward et al. |
| 5,595,662 A | * | 1/1997 | Sanderson ............. 202/234 |
| 5,756,632 A | | 5/1998 | Ward et al. |
| 5,770,086 A | * | 6/1998 | Indriksons et al. ........ 210/643 |
| 5,976,186 A | | 11/1999 | Bao et al. |
| 6,022,376 A | | 2/2000 | Assell et al. |
| 6,264,695 B1 | | 7/2001 | Stoy |

FOREIGN PATENT DOCUMENTS

| | | |
|---|---|---|
| EP | 0 121 099 A2 | 10/1984 |
| EP | 0 353 936 A1 | 2/1990 |
| EP | 0 784 987 A2 | 7/1997 |
| WO | WO 96/01598 A1 | 1/1996 |
| WO | WO 01/22902 A2 | 4/2001 |

\* cited by examiner

*Primary Examiner*—Krishnan S Menon
(74) *Attorney, Agent, or Firm*—Birch, Stewart, Kolasch, and Birch, LLP (57) ABSTRACT

Water-desalination and/or water purification devices. Alternatively, devices that are implantable in animal bodies, possibly configured as self-inflating spinal disc prostheses. The devices include specified types of water-absorbing solute encapsulated by non-porous, water-permeable polymer membranes having specified properties. Also, methods of using the devices in biomedical applications or water treatment.

6 Claims, 6 Drawing Sheets

PRODUCTION OF POTABLE LIQUIDS

This application claims priority under 35 U.S.C. §120 to application Ser. No. 09/986,371, which was filed on Nov. 8, 2001, now U.S. Pat. No. 6,692,528 B2. The entire contents of application Ser. No. 09/986,371 are expressly incorporated by reference. This application also claims priority, under 35 U.S.C. §119(e), to provisional Application Ser. No. 60/246,733, filed Nov. 9, 2000. The entire contents of Application Ser. No. 60/246,733 are expressly incorporated by reference.

FIELD OF THE INVENTION

The present invention provides articles formed from dense polymer membranes and films, which articles spontaneously inflate/expand (or deflate/contract) under the effects of osmotic pressure. By varying the initial volume, molecular weight, solubility, concentration, and temperature of solutions contained within formed articles, the volume of the formed articles and the pressure within the formed articles can be precisely controlled. This invention is therefore useful for many medical, industrial, and consumer applications.

BACKGROUND OF THE INVENTION

U.S. Pat. No. 4,157,085 discloses a surgically implantable device for expanding skin and mucous tissue. The device comprises a partially collapsed sealed envelope formed from a material that is permeable to extracellular body fluids, and a material which establishes an osmotic potential across the envelope wall. As bodily fluid crosses the membrane to fill the envelope, the envelope expands, thereby expanding the adjacent tissue. The envelope material, which ranges from 0.001 to 0.020 inches in thickness, can be formed from such polymers as cellulose acetate, crosslinked polyvinyl alcohol, polyurethane, nylon, ethylene vinyl acetate copolymer, polyolefin, polyvinyl chloride, and silicone rubber. The material used to establish the osmotic potential can be, for instance, sodium chloride, calcium chloride, potassium sulphate, sodium acetate, ammonium phosphate, magnesium succinate, glucose, alanine, vinyl pyrrolidone, carboxymethylcellulose, urea, "blood by-products", proteins, and/or dextran. The amount of expansion material used is selected depending on the desired speed of expansion of the envelope and the desired final volume thereof.

U.S. Pat. No. 5,005,591 points out that the device described in U.S. Pat. No. 4,157,085 has problems. One problem is in the use of silicone as the envelope material. In thicknesses that are adequate for product safety, silicone is relatively impermeable to extracellular water. In order to compensate for the required silicone thickness and allow for timely inflation of the tissue, the implant must contain an inordinately high amount of solute. Another, related problem is that rupture of the implanted envelope results in dispersion of highly concentrated solute into the surrounding tissues.

EP 0 784 987 discloses an inflatable prosthesis that contains a dehydrated substance which forms a gel when mixed with an aqueous solution. The dehydrated substance is a polyacrylamide, polyvinylpyrrolidone, hydroxypropyl methyl-cellulose, polyvinyl alcohol, polyethylene oxide, polypropylene oxide, polyethylene glycol, polylactic acid polyglycolic acid, hydrogel polyurethane, chrondotoin sulfate, hyaluronic acid, alginate, etc. The dehydrated substance is placed within an outer shell constructed from a polydimethyl siloxane, a polyurethane, a polyurethane/polyester copolymer, or another similar viscoelastic material. As shown in FIG. 3 of the publication, after the prosthesis is implanted into the body, an aqueous solution is added to the inner cavity thereof by a syringe. The addition of the aqueous solution combines with the dehydrated substance in the cavity to form a gel within the implant.

U.S. Pat. No. 5,756,632 claims an article comprising a hydrophilic gel with a water content of at least about 35% substantially enclosed within a membrane comprising a biocompatible, hydrophilic, segmented block polyurethane copolymer. The block copolymer comprises about 5 to 45 weight-% of at least one hard segment and about 95 to 55 weight-% of at least one soft segment. The soft segment of the block copolymer comprises at least one hydrophilic, hydrophobic, or amphipathic oligomer selected from the group consisting of aliphatic polyols, aliphatic polyamines, aromatic polyamines, and mixtures thereof. This patent also claims a method of permeating molecules—such as glucose, angiotensin I, glucagon, insulin, aprotinin, albumin, IgG, and oxygen—while substantially preventing the passage of cells and particulate matter between two fluids, using a biocompatible, hydrophilic, segmented block polyurethane copolymer.

U.S. Pat. No. 6,264,695 discloses a spinal nucleus implant for replacement of a portion of nucleus pulposus tissue removed from a spinal disc. The implant is an anisotropically swellable, biomimetic xerogel plastic, having a negatively charged lubricious surface and having a two phase structure with a hydrophobic phase having high crystallinity and low water content and a hydrophilic phase having low crystallinity and high water content. The xerogel plastic is capable of rehydration and of osmotic movement of liquid therethrough in response to osmotic pressure change to thereby increase and decrease liquid content in its hydrated state. Example 1 of the patent molds an acrylonitrile/acrylic acid block copolymer into the shape of a nucleus pulposus, and indicates that when the molded article is implanted into a vertebrate spine, it will be partially hydrated by body fluids, swelling to the shape and tension required for its long-term function. The patent also discloses surgical implant procedures utilizing the disclosed spinal nucleus implant.

SUMMARY OF THE INVENTION

The present invention provides devices that are implantable in animal bodies. In one embodiment, the devices of the present invention include a solute that is encapsulated by a water-permeable polymer membrane. The membrane polymer will ideally be biocompatible, strong and flexible, abrasion resistant, biostable, and highly permeable to water while providing an effective barrier to the solute. The membrane should also be sterile and processable by thermoplastic or solution methods suitable for device fabrication. The solute should be water soluble, non-toxic, and biostable within the internal cavity of the device.

One specific application of the present invention is a self-inflating/shape-memory prosthetic nucleus for percutaneous insertion in a minimally invasive treatment of human spinal disc degeneration. Another embodiment of this invention is a method for treating a spine of a vertebrate which comprises inserting such a device into an area of the spine that contains a degenerated, damage, or missing disc and allowing the device to expand by permeation of aqueous fluid into a cavity containing the solute.

This invention includes the use of a water-permeable polymer (preferably biostable) in the form of a dense membrane with moderate to low water absorption (less than 50 weight-%, preferably less than 15 weight-%, of the combined weight of the polymer and the absorbed water) containing a dispersed polymeric or monomeric solute to fabricate a device or formed article. This invention provides a high strength, dense osmotic membrane containing a low molecular weight solute to produce high osmotic pressure.

In summary, this invention provides a device implantable in an animal (including human) body. The device comprises a water-absorbing solute encapsulated by a non-porous, water-permeable polymer membrane. The membrane has a moisture vapor transmission rate (MVTR) by ASTM Method E96BW greater than 100 g/square meter/day at 1 mil thickness, a dry tensile strength of greater than 500 psi, and a permeability to said solute of less than $10^{-3}$ cm$^2$/sec. In preferred embodiments of this invention, the MVTR minimum may be >1000, >2000, >5000, or >10,000 g/square meter/day at 1 mil thickness, the tensile strength may be >1000, >2000, or >5000 psi, and the permeability may be <$10^{-4}$, <$10^{-5}$, or <$10^{-6}$ cm$^2$/sec. The solute is capable of providing said device with a pressure of approximately 0.1 psi or more for a period of at least 24 hours. In preferred embodiments of this invention, the osmotic pressure that can be held may be >1, >10, or >100 psi and the osmotic pressure can be held at those levels for >1 week, >6 weeks, or >1 year.

In accordance with this invention, each of these parameters may be varied independently. In a particularly preferred device of this invention, the membrane has a moisture vapor transmission rate by ASTM Method E96BW greater than 2000 g/square meter/day at 1 mil thickness, a dry tensile strength of greater than 2000 psi, and a permeability to said solute of less than $10^{-4}$ cm$^2$/sec, and the solute is capable of providing the device with a pressure of approximately 100 psi or more for a period of at least six weeks.

In the devices of this invention, the membrane polymer is preferably a block copolymer having a polyurethane and/or polyurea hard segment and a soft segment selected from the group consisting of polyalkylene oxides, polyalkylene carbonates, polysiloxanes, and linear or branched hydrocarbons. The soft segment is most preferably a polyalkylene oxide soft segment. Devices made in accordance with this invention generally employ membranes having thicknesses within the range 1 to 16 mil.

For some applications, the membrane used to make the devices may have dispersed therein or covalently bound thereto a water-soluble additive, such as sodium chloride, glycerine, or polyethylene oxides. This permits the devices to decrease in permeability over time.

In the devices of this invention, the solute is most preferably a polyacrylamide having a nominal weight-average molecular weight of 1200-3000 Daltons. The solute is normally present in devices of this invention in amounts of 0.1-50 grams, preferably in amounts of 1-3 grams.

In one specific embodiment of this invention, the device is a self-inflating prosthetic spinal disc nucleus. In another specific embodiment, the device is a self-inflating spinal disc nucleus surrounded by a reinforced perimeter and attachment means, configured to form a complete spinal disc prosthesis. A method embodiment of this invention includes treating a spine of a vertebrate by inserting one of these devices into an area of the spine that contains a degenerated, damaged, or missing disc and allowing the device to expand by permeation of aqueous fluid into a cavity containing the solute.

Among contemplated variations of this invention are devices in which the solute comprises a blend of low molecular weight solute for quick inflation of the device and a high molecular weight solute to provide long term pressure and stability and devices in which the membrane decreases in permeability over time to permit rapid short term inflation and persistent long term avoidance of solute leakage.

This invention also provides a method for obtaining sustained maintenance of high pressure in a device implanted in an animal body, said method comprising the steps of: selecting a membrane to have a moisture vapor transmission rate by ASTM Method E96BW greater than 100 g/square meter/day at 1 mil thickness and a dry tensile strength of greater than 500 psi; selecting a solute to be capable of providing said device with a pressure of approximately 0.1 psi or more for a period of at least 24 hours; encapsulating said solute in said membrane to form said device; and implanting said device into said body, whereupon the solute in said device absorbs water from ambient aqueous fluids present in said body until it is inflated to a pressure of approximately 0.1 psi or more. All of the preferred device parameters specified above are relevant to this method. In an especially preferred embodiment, this method comprises the steps of: selecting a membrane to have a moisture vapor transmission rate by ASTM Method E96BW greater than 2000 g/square meter/day at 1 mil thickness and a dry tensile strength of greater that 2000 psi; selecting a solute to be capable of providing said device with a pressure of approximately 100 psi or more for a period of at least six weeks; encapsulating said solute in said membrane to form said device; and implanting said device into said body, whereupon the solute in said device absorbs water from ambient aqueous fluids present in said body until it is inflated to a pressure of approximately 100 psi or more. Inflation to the target pressure can, if desired, be accomplished within a period of 24 hours.

In a non-biomedical context, this invention provides a potable-liquid producing device comprising a water-absorbing solute encapsulated by a non-porous, water-permeable polymer membrane. As above, the membrane has a moisture vapor transmission rate by ASTM Method E96BW greater than 100 g/square meter/day at 1 mil thickness, a dry tensile strength of greater than 500 psi, and a permeability to said solute of less than $10^{-3}$ cm$^2$/sec, and the solute is capable of providing said device with a pressure of approximately 0.1 psi or more for a period of at least 24 hours. As above, each parameter is increased (or in the case of permeability, decreased) in preferred embodiments of the invention. The related method of desalinating and/or purifying water by immersing the device of in a body of water to be desalinated or purified is likewise an aspect of the present invention.

DETAILED DESCRIPTION OF THE INVENTION

Colligative properties are properties that depend on the number of solute particles dissolved in a solvent. There are four colligative properties of solutions: boiling point elevation, freezing point lowering, vapor pressure lowering, and osmotic pressure. An osmotic pressure gradient will cause a solvent to permeate a dense or microporous permeable membrane. In accordance with the present invention, dry solute or a concentrated solution of solute may be placed in the cavity of such a membrane material fabricated into a formed article containing a cavity. In the case that the solute is a dry powder or neutralized or non-neutralized polyelectrolyte, it may take the form of a solid film, a coating, or a pellet, or may be optionally dispersed in a matrix formed from a second polymer.

If the formed article is immersed in a fluid, e.g., blood, or into a fluid-rich "solid", for instance, human tissue, having an osmotic pressure different from that which exists within the cavity, liquid from the fluid or fluid-rich solid—as well as from any solution of solute in the cavity—will permeate the formed article, increasing the article's volume and internal pressure. Measurable permeation and the attendant volume increase will continue until the osmotic pressures on both sides of the membrane are equal. That is, once osmotic pressure equilibrium is reached and maintained, no additional net transfer of solvent into or out of the cavity should occur.

If the membrane is impermeable to solute particles (e.g., atoms, molecules, or ions) or when the solute concentration gradient across the membrane reaches zero, the solute concentration will, thereafter, remain constant inside the cavity of the formed article, assuming that the solute remains constant in molecular weight while in solution (within the cavity). As with the pressure exerted by a gas, the osmotic pressure of a solution ideally depends on the number of "particles" present, but not on their identity.

In accordance with this invention, a formed article (for instance in the shape of a spinal disc nucleus) is fabricated from a water-permeable polymer in the form of a dense membrane or film. The formed article may contain a cavity charged with undissolved solute (in monomeric, oligomeric, or polymeric form), a concentrated solution of one or more solutes, or even a super-saturated solution of solute in the solvent. The cavity may be optionally freed of non-condensable gas, e.g., by displacement or by vacuum treatment. Upon immersion into a solvent-containing phase (e.g., body tissue, bone marrow, or blood) the formed article will increase in size by an amount that is determined, in part, by the molecular weight and concentration of the solute initially contained within the cavity.

It is possible via the design of the formed article, e.g., by the size of the cavity relative to the molal concentration of contained solute, by the choice and thickness of materials of construction, etc., to produce a substantial pressure. This internal pressure could be used to counteract external pressures on the exterior of the formed article. In the example of the spinal disc nucleus, the required internal pressure could be quite high as determined by the load on the spine under different types and intensities of physical activity.

The Polymers

Suitable polymers for the practice of this invention include those disclosed in U.S. Pat. No. 5,428,123 (CO-POLYMERS AND NON-POROUS, SEMI-PERMEABLE MEMBRANE THEREOF AND ITS USE FOR PERMEATING MOLECULES OF PREDETERMINED MOLECULAR WEIGHT RANGE) and those disclosed in U.S. Pat. No. 5,589,563 (SURFACE-MODIFYING ENDGROUPS FOR BIOMEDICAL POLYMERS), the entire contents of both of which patents are hereby expressly incorporated by reference herein.

Polymers useful in the present invention are elastomers, plastics, and reinforced composites that are sufficiently biostable for the intended duration of implantation and that are permeable to water at a rate (per unit thickness) that results in an expansion time that is appropriate in the context of the product (e.g., in clinical use of a device or prosthesis). Expansion time for a specific formed article made from a specific polymer is also determined by the thickness of the polymer through which the water permeates to enter the cavity, that is, by the design of the formed article. It should be noted that the membranes of the present invention are not porous membranes. They are solid membranes configured to be permeable by vapors of aqueous liquids or non-aqueous solvents.

The membrane used in the device of the present invention may be configured to decrease in permeability over time. This would permit rapid short term inflation of the device while allowing for persistent long term avoidance of solute leakage from the device. One way of producing membranes with time-dependent reduction in permeability in accordance with this invention is to disperse a water-soluble additive (e.g., polyethylene oxide) into the membrane polymer before fabricating the membrane. The additive will be dispersible in, or, preferably, thermodynamically compatible with, the membrane polymer, at least in the dry state. The admixture forms a strong membrane (which is often optically clear). Upon hydration as the device is used, the very high level of hydrophilicity caused by the additive increases membrane water absorption and consequently increases the membrane's water permeability. Upon prolonged exposure to aqueous fluid, however, the additive leaches out, thus reducing membrane hydrophilicity and permeability. For use in an implantable device, the additive will be selected to be innocuous, biocompatible, and/or easily excreted from the body. Sodium chloride, polyethylene oxides of various molecular weights, other hydrophilic polymers used in the body, glycerine, and the like, may all be used. For a membrane polymer that contains covalently bonded polyethylene oxide in its backbone (such as BBF-21024, see below), polyethylene oxide is the preferred additive due to its excellent compatibility with the base (membrane) polymer. Other additives may be compatible with specific membrane polymers due to similar solubility parameters, molecular weights, and/or interactions with the membrane polymer, e.g., hydrogen bonding, acid-base, etc. Alternatively (or cumulatively) to admixing the water-soluble polymer into the membrane polymer, one may covalently bind it to the membrane polymer, for instance as end groups, by means of bonds that are subject to scission by hydrolysis, oxidation, and so on. Upon cleavage, the water-soluble polymer is free to leach out of the membrane polymer like an additive.

Some specific polymers that can be used herein are virtually all polyurethane elastomers, crosslinked silicone elastomers, silicone-containing copolymers (vulcanized or thermoplastic), polyolefin elastomers, Kraton elastomers, Hytrel, Pebax, and so on. Virtually any plastic or elastomer, whether thermoplastic or thermoset, which has the required solvent (often water) permeability rate and biostability (if necessary) may be used. Additional requirements for the polymer include of course the strength and processability to be fabricated into the specific device.

An added benefit is that biomedical polymers such as certain silicones, polyurethanes, and other polymers that have a history of successful implantation in the human body may be used. In this way, meeting regulatory requirements for FDA approval and for CE mark will be greatly facilitated.

Polyurethanes and/or polyureas making up the hard segments of the permeable nonporous copolymers which may be used in this invention are preferably made with aromatic or aliphatic diisocyanates, such as diphenylmethanediisocyanate and dicyclohexylmethanediisocyanate, or mixtures thereof. The weight-average molecular weight of the diisocyanate component of the hard segment will typically range from 100 to 500. Polyisocyanates may also be used. These diisocyanates and polyisocyanates may be chain-extended with aliphatic polyols to produce polyurethanes, and/or with aliphatic or aromatic polyamines, such as ethylene glycol, 2-methylpiperazine, isophorone diamine, and mixtures thereof to produce polyureas. The weight average molecular weight of the chain extender component of the hard segments will typically range from 18 to 500. The soft segments of the permeable nonporous copolymers which may be used in accordance with this invention are preferably made with polyfunctional aliphatic polyols or with polyfunctional aliphatic or aromatic amines, such as polyethylene oxides and multi-functional amine-terminated silicones.

A segmented block copolymer based on a biostable aromatic polyurea "hard segment" and an amphipathic (i.e., containing both hydrophobic and hydrophilic segments) "soft segment" provides especially suitable membrane materials for use in the present invention. A preferred embodiment thereof is a polyurethane comprising approximately 27% polyurea hard segment, approximately 72% mixed soft segment containing approximately 24% telechelic polyethylene oxide, and approximately 0.55% semi-telechelic polyethylene oxide and 0.225 silicone endgroups. Such membranes are disclosed in U.S. Pat. No. 5,589,563. This particular membrane is sometimes referred to herein as "BBF 21024".

The Solutes

Net water permeation stops when the osmotic pressure differential across the membrane reaches equilibrium. This can occur simply by solute molal concentration equilibrium with body fluids adjacent to the implant (i.e., an equal number of particles dissolved per unit volume of aqueous solvent) and/or by a combination of osmotic pressure, applied external pressure, and pressure due to expansion of the polymer used to fabricate the formed article as the formed article absorbs water. In any case, the size of the expanded implant may be carefully regulated by the concentration of solute contained within the polymer device and by the physical and mechanical properties of the (hydrated) water-permeable polymer. Using this approach, a high ratio of expanded-to-collapsed dimensions can be obtained (relative to hydrogels) while simultaneously presenting a biostable polymer to the device-body interface.

It should be noted that as the membrane is stretched by the ingress of (e.g., aqueous) solvent, it will increase the pressure within the cavity, which may contain some trapped gas as well as liquid solution. The instantaneous pressure within the cavity would be affected by the external load, by the dimensions and tensile properties of the material of construction of the cavity, by membrane (polymer) thickness and modulus, by the initial solute concentration, by the extent of approach to equilibrium, and by the temperature and the amount of compressible gas contained within the cavity. However, once the osmotic pressure on both sides of the membrane becomes equal, no additional dimensional changes will occur in the formed article, at least in the absence of membrane creep or degradation.

To minimize back diffusion through the wall of the device, and attendant loss of internal osmotic pressure, high molecular weight solutes would be preferred, except that their molal concentration per unit volume is low. That is, the internal osmotic pressure than can be generated per unit weight of a candidate solute at body temperature will be determined by the mass and molecular weight of the solute and by the ultimate internal volume of the device.

A low molecular weight water-soluble linear polyacrylamide polymer (nominal weight average molecular weight=1500) is a preferred solute in accordance with the present invention. The nominal 1500 MW polyacrylamide is sold in solution form, 50% by weight in water. Like all synthetic polymers it has a polydisperse molecular weight distribution constituting a statistical distribution of polyacylamide chain lengths. It has been determined that some low molecular weight species are present in the commercially available polymer. These initially give a very high osmotic pressure, due to the high molality that the produce. However, they soon permeate the polymer membrane and escape from the cell interior. Accordingly, purification may be necessary before it can be used in this invention.

The solute solution can be purified by dialysis using, for example, cellulosic dialysis membranes. An additional aspect of the present invention, however, contemplates preparing a solute, e.g. a polyacrylamide polymer, for use in a prosthesis by dialysis using thin membranes of substantially the same chemistry as the polymer that will be used to manufacture the prosthesis. This ensures that all permeable species are removed from the solute before using it to fill the device. Alternatively, polymer fractionation can be performed by a variety of techniques based on differential solubility, sedimentation, diffusion, or chromatographic exclusion. Fractional precipitation or fractional solution often provide good separation efficiency and high yields.

The implantable devices of the present invention can be made with a "cocktail" of solutes, that is, with two or more different solutes, each of which contributes different attributes to the device. For instance, one can use a solute blend of a low molecular weight solute for quick inflation of the device and a high molecular weight solute to provide long-term pressure and stability to the device once it is inflated in the body. Of course, if the low molecular weight solute is expected to be able to permeate out through the membrane of the device into the body, it should be a biologically innocuous substance such as sodium chloride.

Configurations

Devices in accordance with this invention may be fabricated by virtually all of the commonly-used techniques of polymer conversion. A suitable polymer can, for instance, be injected into a mold to form a pocket-shaped object. The pocket can then be filled with a suitable solute and sealed, for instance by radio frequency (RF) welding. The solute may be aqueous, or it may be, for example, dried polyacrylamide. Alternatively, the polymer may be cast into a film, and pockets can then be formed from the film, filled with solute, and sealed.

Another embodiment of this invention is a solute dispersed in a matrix polymer contained within the cavity of a device or article formed of the same polymer or of another polymer.

In yet another embodiment, an optionally reinforced polymer is used to fabricate a device containing one or more cavities containing a solute in a specific quantity. Upon insertion in the body, the device expands as water permeates the water-permeable polymer under the effects of osmotic pressure. Suitable reinforcements for the polymer include woven or knitted fabrics, particulate fillers, chopped fiber, and other such types of reinforcement that do not reduce the water permeation rate of the polymer below the minimum acceptable range. Woven or knitted fabric impregnated with the membrane polymer is preferred in this context, since the extent of expansion of the device can be limited even at high internal pressures.

The density of the dry solute together with its osmotic pressure per unit weight will determine the volume occupied by solute in the collapsed device, thereby placing a lower limit on the size of the device during insertion.

Specific Applications

The present invention has many applications in medical, industrial, and consumer products. Because of the wide range of applications of the present invention, the rate as well as the final extent of dimensional changes required for a specific application can vary dramatically. Those skilled in the art will know how to control these variables by the choice of membrane polymer and the size of the cavity and by the amount of solute initially changed within the cavity.

Some examples of formed articles that may be made with biostable semi-permeable membrane materials in accordance with the present invention include prosthetic spinal disc nuclei, prosthetic spinal discs, vascular grafts, aneurism repair devices, vascular stents, cervical dilation devices, breast implants, tissue expansion devices, orthopedic implants, bone fixation devices, vascular occlusion devices, devices for the treatment of male erectile disfunction, male and female incontinence devices, male and female sterilization devices, drug delivery devices, plastic and cosmetic surgery devices, hernia repair devices, intraocular lenses, ophthalmic devices, and water desalination devices.

Water desalination devices will generally not, of course, be implantable. However, otherwise they embody the principles of this invention. For example, a non-toxic solute with optional nutritional value (e.g., glucose, sucrose, fructose, etc.) may be enclosed within a membrane that has low-to-zero permeability to microbes, sodium chloride, and other dissolved or suspended matter found in sea water, brackish water, or fresh water. The contained solute creates a higher osmotic pressure within the device than exists in the water external to the device. Therefore a net flow of water occurs, filling the device. As water enters the optionally deflated device, it forms a potable solution by dissolving or diluting the enclosed solute. Such a device may be used to provide drinking water for extended expeditions away from potable water sources (e.g., back country camping trips) or in emergency situations such as shipwrecks. As an added benefit, the microbial barrier properties of dense membranes will ensure that the potable solution formed within the device is sterile and/or essentially free of disease-causing microbes.

Figure 5A:
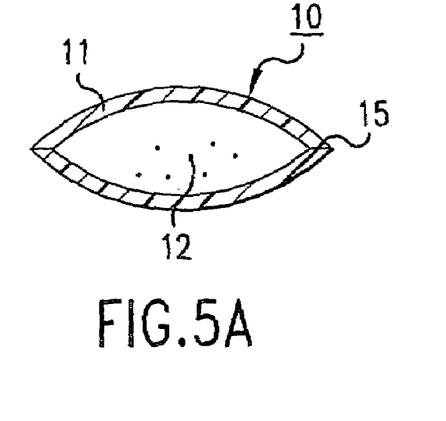
FIG. 5A presents a cross-sectional schematic view of an uninflated device of the invention.
Figure 5B:
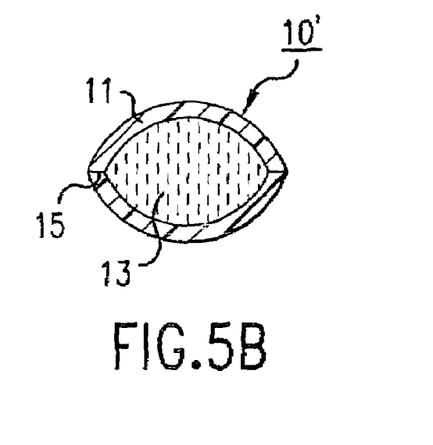
FIG. 5B presents a cross-sectional schematic view of an inflated device of the invention.
Figure 6A:
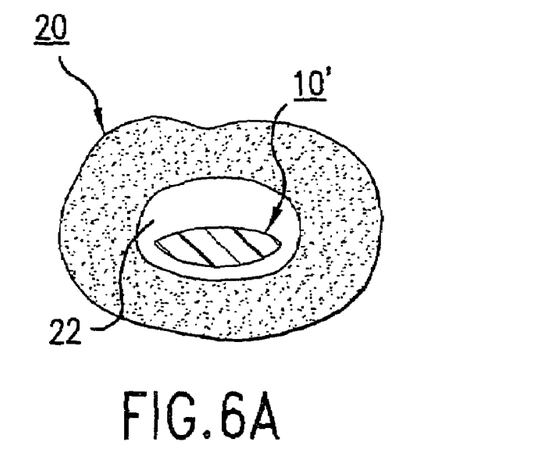
FIG. 6A presents a cross-sectional schematic view of a spinal in which is located an uninflated device of the invention.
Figure 6B:
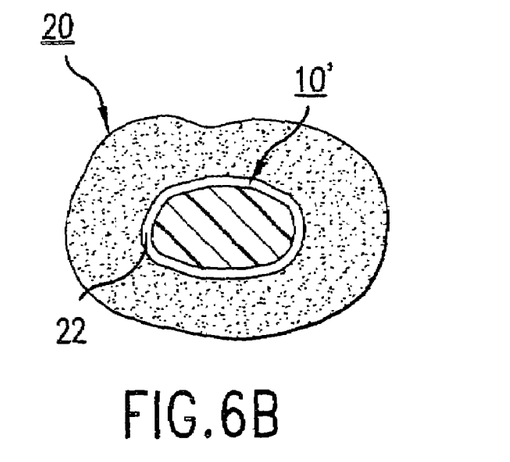
FIG. 6B presents a cross-sectional schematic view of a spinal in which is located an inflated device of the invention.
Figure 7A:
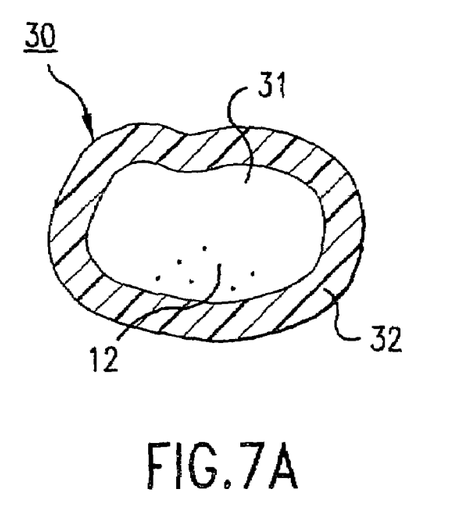
FIG. 7A presents a cross-sectional schematic view of an uninflated spinal disc prosthesis of the invention.
Figure 7B:
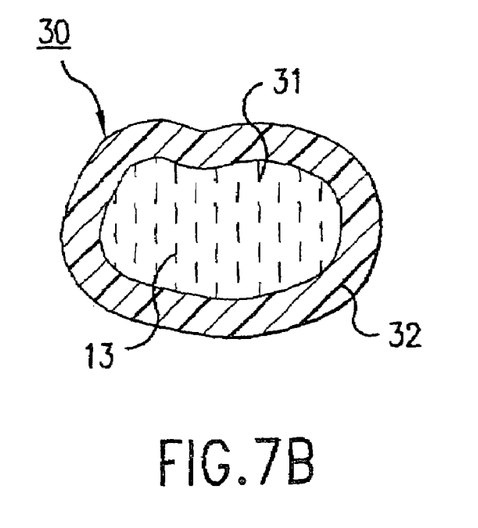
FIG. 7B presents a cross-sectional schematic view of an inflated spinal disc prosthesis of the invention.

Two particularly preferred embodiments of this aspect of the invention are a self-inflating prosthetic spinal disc nucleus (FIGS. 5 and 6) and a self-inflating spinal disc nucleus surrounded by a reinforced perimeter and attachment means, configured to form a complete spinal disc prosthesis (FIG. 7). FIG. 5A presents a cross-sectional schematic view of an uninflated device (10) comprising a polymeric membrane (11) with RF welds (15) encapsulating a solute (12). FIG. 5B presents a cross-sectional schematic view of an inflated device (10') comprising a polymeric membrane (11) with RF welds (15) encapsulating an aqueous solution of the solute (13). FIG. 6A presents a cross-sectional schematic view of a spinal disc (20) having a cavity (22) in which is located an uninflated device (10). FIG. 6B presents a cross-sectional schematic view of a spinal disc (20) having a cavity (22) in which is located an inflated device (10'). FIG. 7A presents a cross-sectional schematic view of a spinal disc prosthesis (30) having: a cavity (31) in which is located solute (12); a reinforced perimeter (32); and attachment means (not shown). FIG. 7B presents a cross-sectional schematic view of a spinal disc prosthesis (30) having: a cavity (31) in which is located an aqueous solution of the solute (13); a reinforced perimeter (32); and attachment means (not shown).

Biodegradable/Bioresorbable Embodiments

In addition to biostable polymers it is possible to fabricate formed articles of the present invention from permeable biodegradable/bioresorbable polymers. The membranes comprising such formed articles expand as described above, but will eventually degrade and be resorbed into and excreted from the body, or otherwise safely enter the environment. Upon degrading, the formed article may eventually rupture or otherwise release the solution contained within it into the body. Therefore in this embodiment of the invention, innocuous fluids are used to provide the solutions that generate the osmotic pressure differential. Some examples of suitable fluids are normal saline solutions, glucose solutions, glycerol solutions, and other such metabolizable solutions that are safely tolerated by humans and the environment.

Bioresorbable semi-permeable membrane materials may be used in accordance with the present invention for instance in tissue scaffolds for tissue engineering implants, vascular occlusion devices, anastomotic devices, drug delivery devices, wound closure devices, implants for preventing post-surgical adhesion, temporary cardiac assist devices, and vascular grafts.

EXAMPLES

One such application is the creation of medical devices and prostheses to be implanted within the human body. For instance, a prosthetic nucleus for a spinal disc, which can be implanted by standard surgical techniques or, preferably, by so-called minimally invasive procedures, can be prepared in accordance with the present invention. Upon insertion and placement within the vertebral body, the disc or nucleus would expand/inflate under the effects of osmotic pressure by permeation of aqueous fluid from the surrounding blood or tissue. During this process, the osmotic pressure of the region surrounding the implant would be maintained roughly constant by the normal homeostasis of the body.

Optionally the region neighboring the implant may be supplied with supplemental fluid by injection or irrigation.

For applications in which rapid inflation is desired, e.g., directly after implantation in the body, a source of water, other solvent, or solution may be supplied to the interior cavity of the device by injection through a self-sealing septum or a one-way or two-way valve and/or by piercing the dense membrane itself. In the latter case, the membrane would normally be resealed after the injection. Following the injection of water or solvent for the purpose of increasing size, continued transport of water or solvent driven by osmosis will determine the final internal pressure. In many applications, the final pressure is higher than that created by an initial injection.

Osmotic Capability

Figure 4:
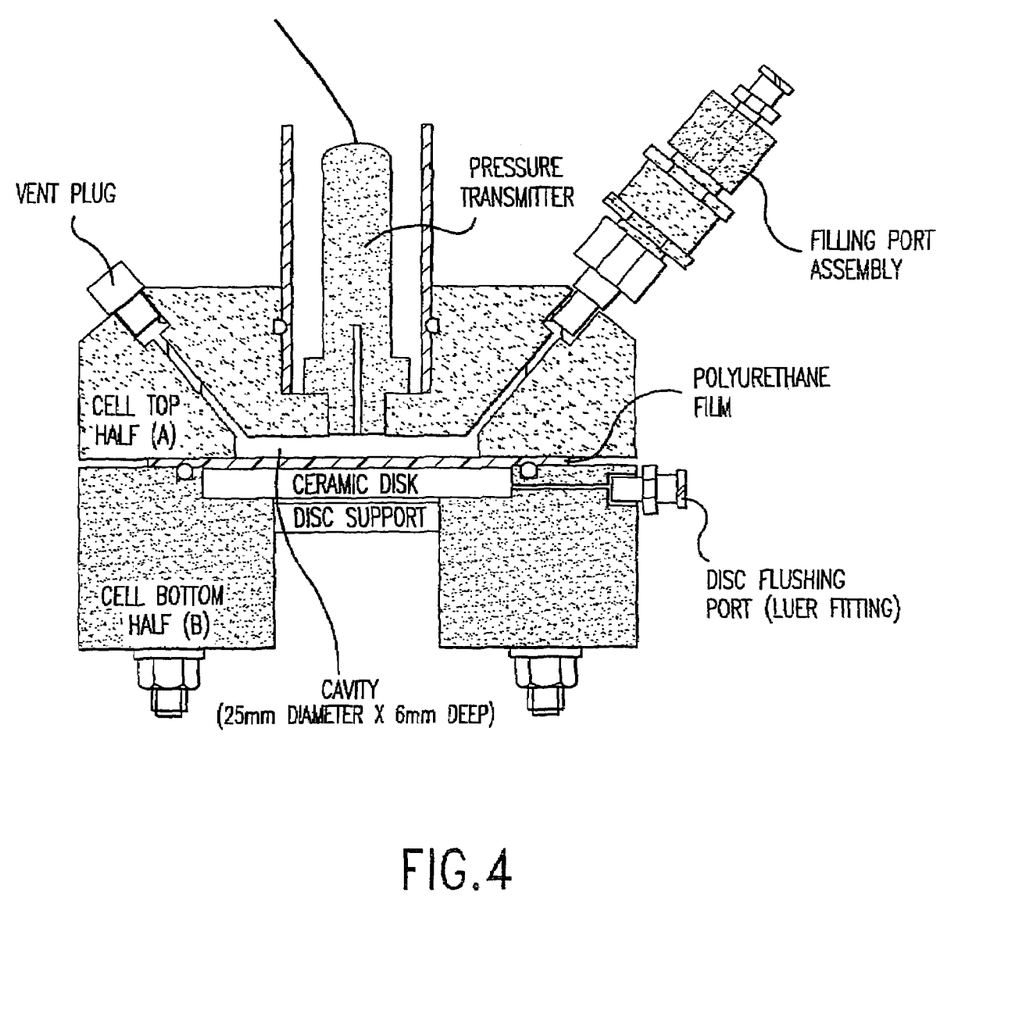
FIG. 4 is a schematic depiction of a stainless steel test cells used to test devices made in accordance with the present invention.

Stainless steel test cells as shown schematically in FIG. 4 were used to characterize the osmotic potential of polyacrylamide contained behind a BBF 21024 membrane. The cell cavities were filled with polyacrylamide/water solutions and placed into heated waterbaths. The concentrations tested were 25% and 50% polyacrylamide by weight in water. The 25% solution was prepared by evaporating water from the 50% polyacrylamide solution, then taking the dry polyacrylamide and adding distilled water. Pressure was recorded every 10 minutes. The test results are shown graphically in FIGS. 1 and 2.

Figure 1:
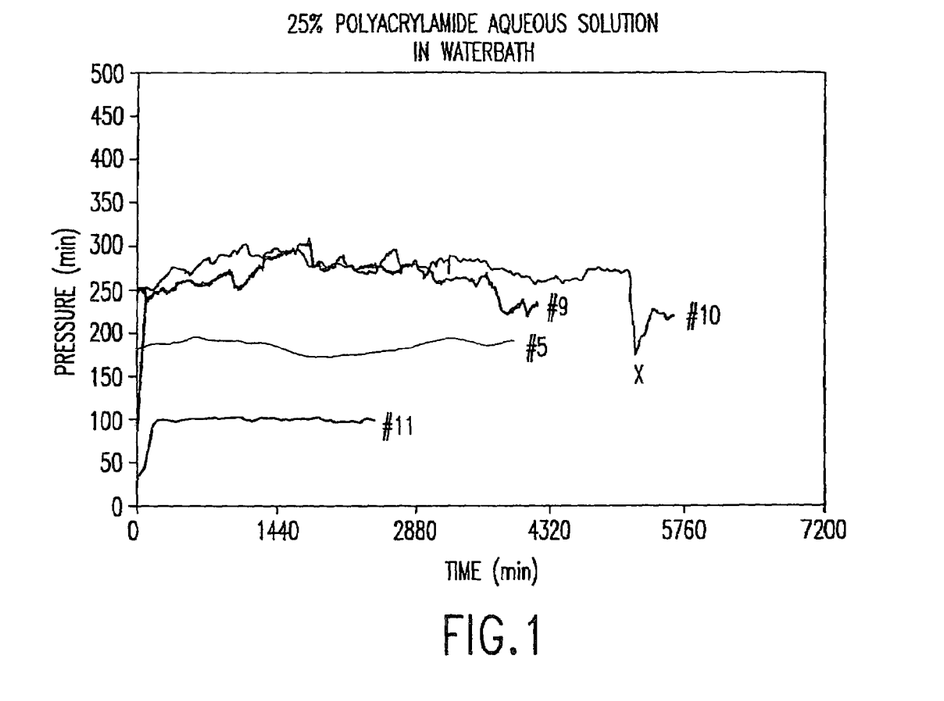
FIGS. 1 and 2 are graphic depictions of pressure tests results demonstrating advantages of this invention.
Figure 2:
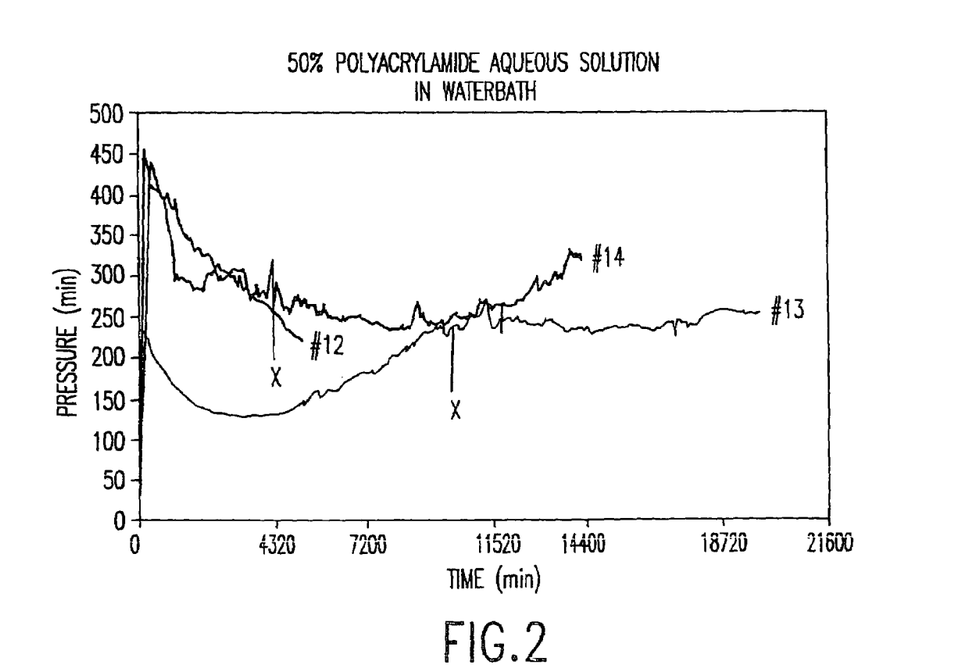

As depicted in FIG. 1 for the 25% solution, four runs are reported, identified as #5, #9, #10, and #11. For run #9, starting data was lost during a power outage. For run #10, the temperature drop at the point on the curve marked with an "X" was due to changing the water in the waterbath. The stabilized pressures ranged from 100-275 psi, with peak pressure around 300 psi. The average stable pressure was about 178 psi. As depicted in FIG. 2 for the 50% solution, three runs are reported, identified as #12, #13, and #14. For runs #13 and #14, the temperature drops at the points on the curves marked with an "X" were due to changing the water in the waterbath. The stabilized pressures converged around 250 psi. The highest pressure for the 50% solution peaked at 450 psi, then declined and stabilized around 250 psi. These result demonstrate that pressures within the range of clinical use are achieved by the present invention.

Variability in the data collected can be attributed to several factors. Small variations in the thickness of the membrane, pinholes in the membrane, rust formed in the waterbath during some of the test runs, variations in the manufacture of the test cells, and settling of undissolved solute within the test cell could all affect the pressure results. Another possible contributor to the data variations is believed to be the molecular weight dispersity of the polyacrylamide. The polyacrylamide used was determined to have an average molecular weight of approximately 2500 Daltons, with a range of 400-30,000 Daltons.

Polyacrylamide Retention

If the polyacrylamide solute were to pass through the semi-permeable membrane, this would cause a device to lose pressure over time. It was demonstrated that polyacrylamide does in fact stay entrapped behind the membranes used in this invention.

Figure 3A:
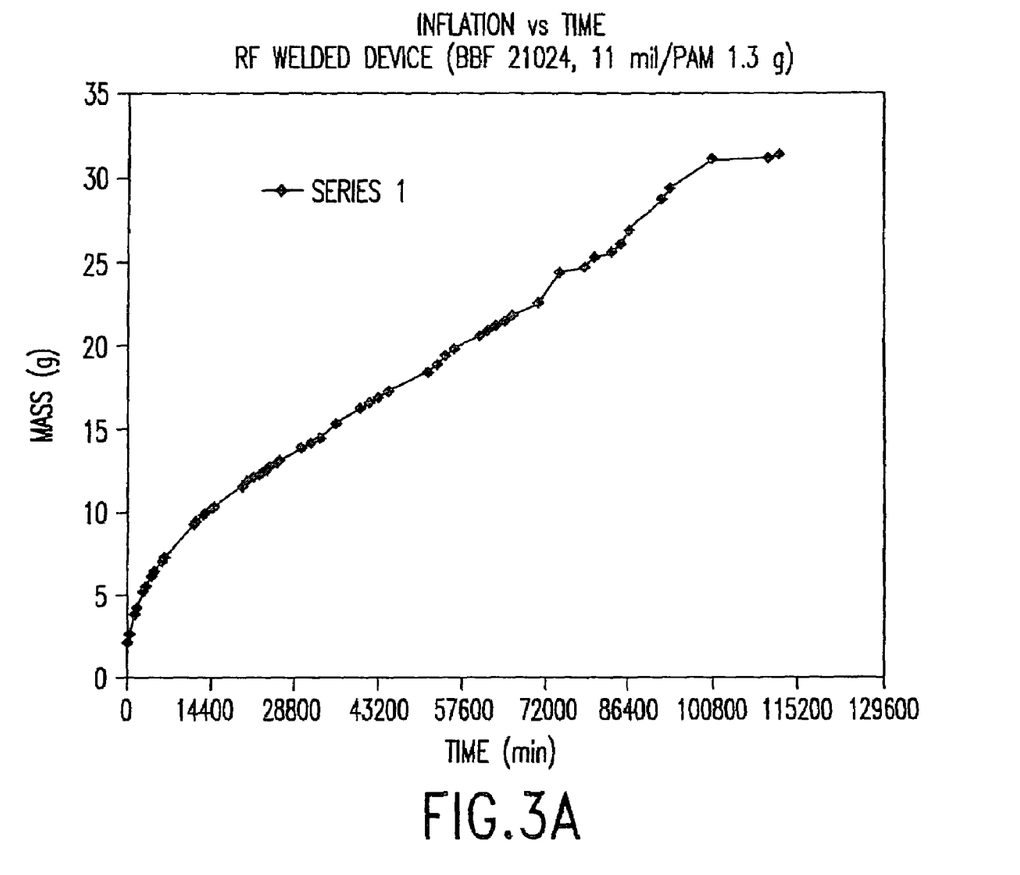
FIG. 3A is a graphic depiction of mass retention results (pressure profile) demonstrating properties of this invention.

One and three tenths grams of polyacylamide (PAM) was encapsulated between two sheets of BBF 21024 membrane within a circular radiofrequency (RF) weld. Excess membrane outside of the weld line was trimmed away, providing an RF welded device in accordance with this invention. The device was submerged in an aqueous sodium chloride solution buffered to a pH of about 7.4+ with sodium bicarbonate. This solution is sometimes referred to as an HBSS solution. The device was dried and weighed over time. Over the course of 80 days, pressure rose and leveled off at about 32 grams—see FIG. 3A. This pressure profile provides clear evidence that PAM does not pass through the membrane.

Figure 3B:
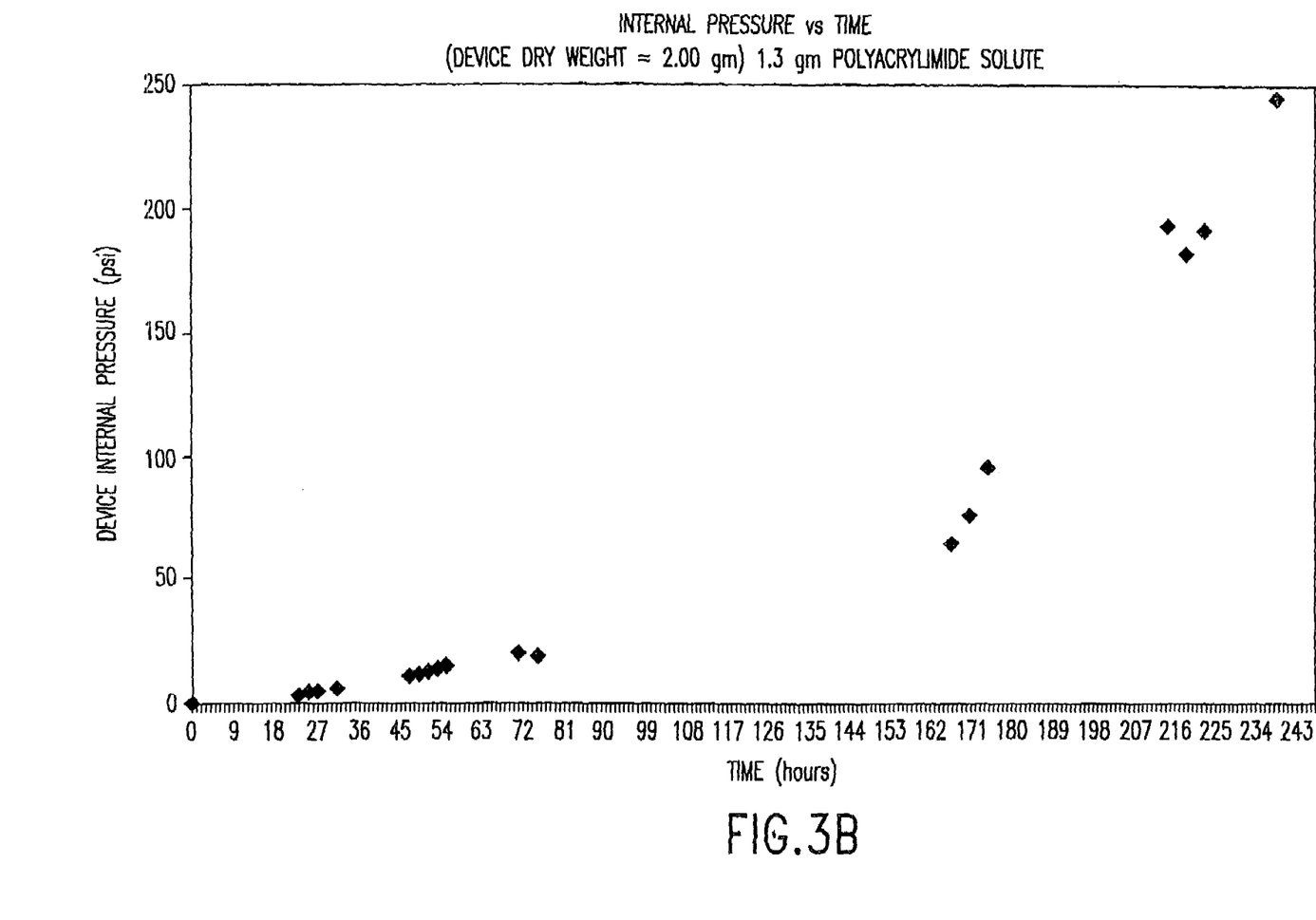
FIG. 3B is a graphic depiction of pressure test results (weight-lifting) obtained in accordance with this invention.

One and three tenths grams of polyacylamide was encapsulated between two sheets of BBF 21024 membrane within a circular RF weld. Excess membrane outside of the weld line was trimmed away, providing an RF welded device in accordance with this invention. The device, which weighed 2.00 grams dry, was submerged underwater in plain water, using a weight. The test chamber was a 5 mm by 35 mm cylinder (4.81 cc). The height that the weight traveled was recorded over time. The height, weight, and area were used to calculate the psi required to lift the weight. The results are reported in FIG. 3B.

Inflation Study

A pouch weighing 0.77 grams was prepared from BBF 21024 film 11 mil in thickness. 1.34 grams of polyacrylamide (having a nominal molecular weight of 1500) in powder form was placed into the pouch, and the pouch was sealed shut with radio frequency radiation. An aqueous sodium chloride solution was buffered to a pH of about 7.4+ with sodium bicarbonate. The pouch was then place into a bath of the buffered salt solution at ambient temperature, and the mass of the pouch, polyacrylamide, and any absorbed water was recorded periodically. The mass of the pouch, polyacrylamide, and absorbed water after various elapsed times are reported in Table I.

TABLE I

| Elapsed time (minutes) | Mass of BBF pouch, polyacrylamide, and water | Water (mL at 20° C.) |
|---|---|---|
| 0 | 2.11 | 0 |
| 360 | 2.61 | 0.497 |
| 1390 | 3.80 | 1.680 |
| 2840 | 5.14 | 3.012 |
| 6445 | 7.18 | 5.040 |
| 12165 | 9.44 | 7.286 |
| 20455 | 11.71 | 9.542 |
| 24775 | 12.67 | 10.497 |
| 30545 | 13.86 | 11.680 |
| 36295 | 15.24 | 13.051 |
| 45275 | 17.15 | 14.950 |
| 55045 | 19.32 | 17.107 |
| 75125 | 24.36 | 22.117 |
| 84050 | 25.61 | 23.359 |
| 92900 | 28.71 | 26.440 |
| 111380 | 31.16 | 28.876 |
| 124985 | 30.46 | 28.180 |
| 134685 | 27.37 | 25.108 |
| 156295 | 24.53 | 22.285 |
| 166475 | 18.63 | 16.421 |

This experiment demonstrates that a device of the present invention absorbs water rapidly (absorbing approximately its own weight in water in 24 hours, i.e., 1440 minutes). Absorption with this particular system peaks at 75-80 days (108,000-115,200 minutes) and then slowly drops off. This decrease in the amount of water retained in the device is believed to be due to low molecular weight polyacrylamide species permeating out through the BBF membrane. For this reason, normally only polyacrylamide or other solutes that have been pre-treated to remove low molecular weight species would actually be used in a biological application.

The invention being thus described generically and with reference to specific embodiments, it will be readily apparent to those skilled in the art that the same may be varied in many ways. All such variations are encompassed by the spirit of the invention, the patented scope of which is demarcated in the appended claims.

What is claimed is:

1. A device for producing potable liquid, said device comprising a water-absorbing solute encapsulated by a non-porous, water-permeable polymer membrane,
   wherein said polymer includes hydrophilic segments or blocks and comprises a member selected from the group consisting of polyurethane elastomers, crosslinked silicone elastomers, thermoplastic silicone-containing copolymers, polyolefin elastomers, styrene-diene copolymers, polyester-polyether copolymers, and polyamide-polyether copolymers,
   wherein said polymer membrane has a moisture vapor transmission rate by ASTM Method E96BW greater than 100 g/square meter/day at 1 mil thickness, a dry tensile strength of greater than 500 psi, and a permeability to said solute of less than $10^{-3}$ cm$^2$/sec, and
   wherein said water-absorbing solute is capable of providing said device with a pressure of approximately 0.1 psi or more for a period of at least 24 hours.

2. The potable-liquid producing device of claim 1, wherein said membrane has low-to-zero permeability to microbes, sodium chloride, and other dissolved or suspended matter found in sea water, brackish water, or fresh water and wherein said solute is a non-toxic solute with nutritional value.

3. The potable-liquid producing device of claim 2, wherein said solute comprises glucose, sucrose, or fructose.

4. A device for producing potable liquid, said device comprising a water-absorbing solute encapsulated by a non-porous, water-permeable polymer membrane,
   wherein said membrane has a thickness of 0.001 to 0.016 inch and said polymer is a block copolymer having a polyurethane and/or polyurea hard segment and a soft segment selected from the group consisting of hydrophilic blocks, polyalkylene oxides, polyalkylene carbonates, poly-siloxanes, and linear or branched hydrocarbons,
   wherein said membrane has a moisture vapor transmission rate by ASTM Method E96BW greater than 100 g/square meter/day at 1 mil thickness, a dry tensile strength of greater than 500 psi, and a permeability to said solute of less than $10^{-3}$ cm$^2$/sec, and
   wherein said solute is capable of providing said device with a pressure of approximately 0.1 psi or more for a period of at least 24 hours.

5. A method for desalinating and/or purifying water which comprises immersing the device of claim 1 in a body of water to be desalinated or purified, thereby producing a desalinated or purified potable-liquid.

6. A method for desalinating and/or purifying water which comprises immersing the device of claim 4 in a body of water to be desalinated or purified, thereby producing a desalinated or purified potable-liquid.

* * * * *